(12) United States Patent
Hernandez et al.

(10) Patent No.: US 7,472,703 B2
(45) Date of Patent: Jan. 6, 2009

(54) VENTILATION COMFORT INTERFACE

(75) Inventors: Shara Hernandez, Davie, FL (US);
Bruce Sher, Lighthouse Point, FL (US)

(73) Assignee: Innomed Technologies, Inc., Coconut Creek, FL (US)

( * ) Notice: Subject to any disclaimer, the term of this patent is extended or adjusted under 35 U.S.C. 154(b) by 521 days.

(21) Appl. No.: 10/967,252

(22) Filed: Oct. 19, 2004

(65) Prior Publication Data

US 2006/0081251 A1    Apr. 20, 2006

(51) Int. Cl.
*A62B 18/02* (2006.01)
*A62B 18/08* (2006.01)
(52) U.S. Cl. .............................. 128/206.21; 128/206.24
(58) Field of Classification Search ............ 128/206.21, 128/0.23–0.25, 0.27, 0.28, 207.11, 207.13
See application file for complete search history.

(56) References Cited

U.S. PATENT DOCUMENTS

| 4,940,043 A * | 7/1990 | Burns et al. .................... 602/18 |
| 5,794,617 A * | 8/1998 | Brunell et al. ......... 128/206.16 |
| 7,234,466 B2 * | 6/2007 | Kwok et al. ........... 128/207.11 |
| 2003/0168063 A1 * | 9/2003 | Gambone et al. ...... 128/203.16 |
| 2006/0130845 A1 * | 6/2006 | Schegerin .............. 128/206.28 |

* cited by examiner

*Primary Examiner*—Justine R Yu
*Assistant Examiner*—Kristen C Matter
(74) *Attorney, Agent, or Firm*—Maier & Maier, PLLC

(57) ABSTRACT

A soft material replaceably coupled to a ventilation interface, wherein the soft material is positioned between the interface and a user's face to alleviate discomfort. The soft material may be configured to be replaceably couple to various ventilation interfaces which may include CPAP interfaces.

18 Claims, 5 Drawing Sheets

VENTILATION COMFORT INTERFACE

FIELD OF THE INVENTION

Exemplary embodiments of the invention are directed to a ventilation interface, and more particularly, to a ventilation interface including a soft material positioned between the interface and a user's face.

DISCUSSION OF THE INVENTION

Obstructive sleep apnea syndrome, commonly referred to as obstructive sleep apnea, sleep apnea syndrome, and/or sleep apnea, is a medical condition whereby one has prolonged episodes of breathing cessation during sleep. During a wakeful period, the muscles of the upper part of the throat passage of an individual keep the passage open, thereby permitting an adequate amount of oxygen to flow to the lungs. During sleep, the throat passage is narrowed due to the muscles in the throat relaxing. In those individuals having a relatively smaller sized throat passage, the narrowed throat passage prohibits the adequate amount of oxygen from flowing into the lungs. Additionally, one or more nasal obstructions, a relatively large tongue, and/or certain shapes of the palate and/or jaw of an individual further prohibit the adequate amount of oxygen from flowing into the lungs.

An individual having the above-discussed conditions can stop breathing for one or more prolonged periods of time, each period of time being up to ten seconds or more. The prolonged periods of time during which breathing is stopped, or apneas, are generally followed by sudden reflexive attempts to breathe. The reflexive attempts to breathe are generally accompanied by a change from a relatively deeper state of sleep to a relatively lighter state of sleep. As a result, the individual suffering obstructive sleep apnea syndrome generally experiences fragmented sleep and this fragmented sleep is not restful. The fragmented sleep further results in one or more of excessive and/or inappropriate daytime drowsiness, headache, weight gain or loss, limited attention span, memory loss, poor judgment, personality changes, lethargy, inability to maintain concentration and/or depression.

Other medical conditions can also prevent individuals, including adults and infants, from receiving adequate amounts of oxygen into the lungs. For example, an infant who is born prematurely can have lungs that are not developed to an extent necessary to receive the adequate amount of oxygen. Further, prior to, during or subsequent to certain medical procedures or medical treatments, individuals can be unable to receive the adequate amount of oxygen.

Under these circumstances, it is known to use a ventilation interface to apply a positive pressure to the throat of the individual, thereby permitting the adequate amount of oxygen to flow into the lungs. In the known ventilation interface, oxygen and/or room air containing oxygen is delivered through the mouth and/or nose of the individual. Known types of positive pressure applied by the known ventilation interface include continuous positive airway pressure (CPAP) in which a positive pressure can be maintained in the throat through a respiratory cycle. Bi-level positive airway pressure (BiPAP) occurs when a relatively high positive pressure is maintained during inspiration and a relatively low positive pressure is maintained during expiration. Intermittent mechanical positive pressure ventilation (IPPV) is also known in which a positive pressure is applied when apnea is sensed (i.e., the positive airway pressure is applied intermittently or non-continuously). One known treatment for the application of such positive pressures includes a conventional face mask that covers the mouth and/or nose and a conventional pair of nasal pillows that are inserted into corresponding nares of the naris.

The conventional mask requires a harness, such as a headband or other gear components to provide and maintain a required fluid- or gas-tight seal between the mask and the face of the individual. Thus, the use of a conventional harness results in a number of disadvantages. For example, because pressure must be applied between the required harness and the head of the individual to maintain the required seal, the harness can be uncomfortable, particularly during sleeping. This discomfort may exacerbate the sleep apnea condition causing more periods of wakefulness. The applied pressure often results in undesirable irritation and sores caused by movement of the mask and harness during periods of both wakefulness and sleep. Further the required seal is generally unable to be maintain when the mask and harness is moved. The mask also generally applies an undesirable pressure to the sinus area that is adjacent to the nose, causing the nasal sinus airways to narrow, thereby increasing a flow velocity through the upper anatomical airways and decreasing lateral pressure against the nasal mucosal walls. The above discussed combination of increased flow velocity and decreased pressure results in the removal of moisture from the mucosal walls during inspiration, causing an undesirable drying and burning sensation in the nares of the patient. As a result, the individual may remove the mask to relive these discomforts, consequently discontinuing the beneficial application of the positive airway pressure.

The conventional nasal pillows include pillow-style nasal seals that are pressed against the bottom portion of the nares. However, the known nasal pillows also require the use of a harness the keep the nasal pillows pressed against he bottom of the nares, resulting in disadvantages similar to those of the conventional face mask.

Other methods of dealing with the discomfort of CPAP masks have been suggested but include limitations that decrease the quality of life for the user. Physicians have recommended applying petroleum jelly to the portion of the mask when irritation occurs. This solution, however, fails because of other discomforts associated with having petroleum jelly on the user's face. Additionally, the mask is more prone to sliding when petroleum jelly is used, thus leading to more potential discomfort and the possibility of losing the necessary air and liquid-tight seal between the mask and the user's face. Further the mask must be cleaned every day when petroleum jelly is applied, which is an undesirable outcome for the user. Another solution has been to intermittently discontinue use of the mask when there is discomfort or irritation. This prevents the user from enjoying the benefits of the mask and offers no guarantee of future comfort to the user.

Other solutions to relieve irritation such as loosening the mask, trying another size of mask and trying another type of mask provide additional disadvantages for the user. Loosening the mask creates problems with the seal between the mask and the user's face, potentially limiting the effectiveness of the mask. Trying other sizes or types of masks may create expenses that the user may not desire to incur. Further, some users may have facial structures or skin conditions that do not lend themselves to any particular size or shape of mask. Greatly improving the comfort of readily available masks is a necessity for these users.

Adjusting the fitting of masks or trying alternative masks can also exacerbate the problem users of these masks are trying to remedy. People who have suffered facial injuries require a properly fitting mask that can be comfortably worn for long durations. These people also desire to avoid having the mask adhere directly to their skin with blood or sweat, which creates additional irritation. People with sleep apnea may also desire to use a certain type of mask in order to avoid interfering with blood circulation in the nasal area. As such, switching masks or adjusting the mask's fitment may be counter-productive for these subjects. Thus a mask which can be comfortably worn without creating additional problems or irritations is desired.

SUMMARY OF THE INVENTION

The present invention provides an improved CPAP mask that allows a user to wear a mask without experiencing discomfort. According to an exemplary embodiment, a moleskin or similarly soft material, comfort cover is affixed to the CPAP mask providing a comfortable fit of the mask to the user's face.

According to another aspect of the present invention, a moleskin or similarly soft material comfort cover may be applied to a ventilation mask in such a manner as to fit flush with the cushion on the ventilation mask. The moleskin may incorporate an elastic band attached to the perimeter of the comfort cover, allowing the comfort cover to be attached to the cushion of the ventilation mask. The comfort cover then may fit snugly on the cushion and conform to the contours of the user's face, allowing for an air and/or liquid-tight seal between the face of the user and the mask.

In a further embodiment of the invention, a comfort cover may be elastically attached to the outside cushion of a mask designed to deliver oxygen to a user or remedy a user's breathing difficulties. A moleskin covering, as one non-limiting example, may be designed so as to be able to attach to a variety of shapes of masks and can be fitted to triangular, circular or other shaped masks.

These and other advantages, objects, features and characteristics of exemplary embodiments of the present invention as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

CPAP masks may be strapped tightly to the face. Strapping the mask tightly to the face can cause rubs and abrasions resulting in discomfort and loss of the sleep-apnic effect. A moleskin or similar soft material can be cut to fit various masks. The moleskin may be cut in the shape of all or some cushions that come in contact with the skin. Precut moleskin or similar soft material could lie between all the contact points of full face mask or nasal mask, or any other device used for treatment of sleep apnea to help seal the mask so that none of the positive airway pressure is lost. Further, the moleskin may prevent abrasions and skin irritations caused by contact with a tightly fitted mask.

Figure 1:
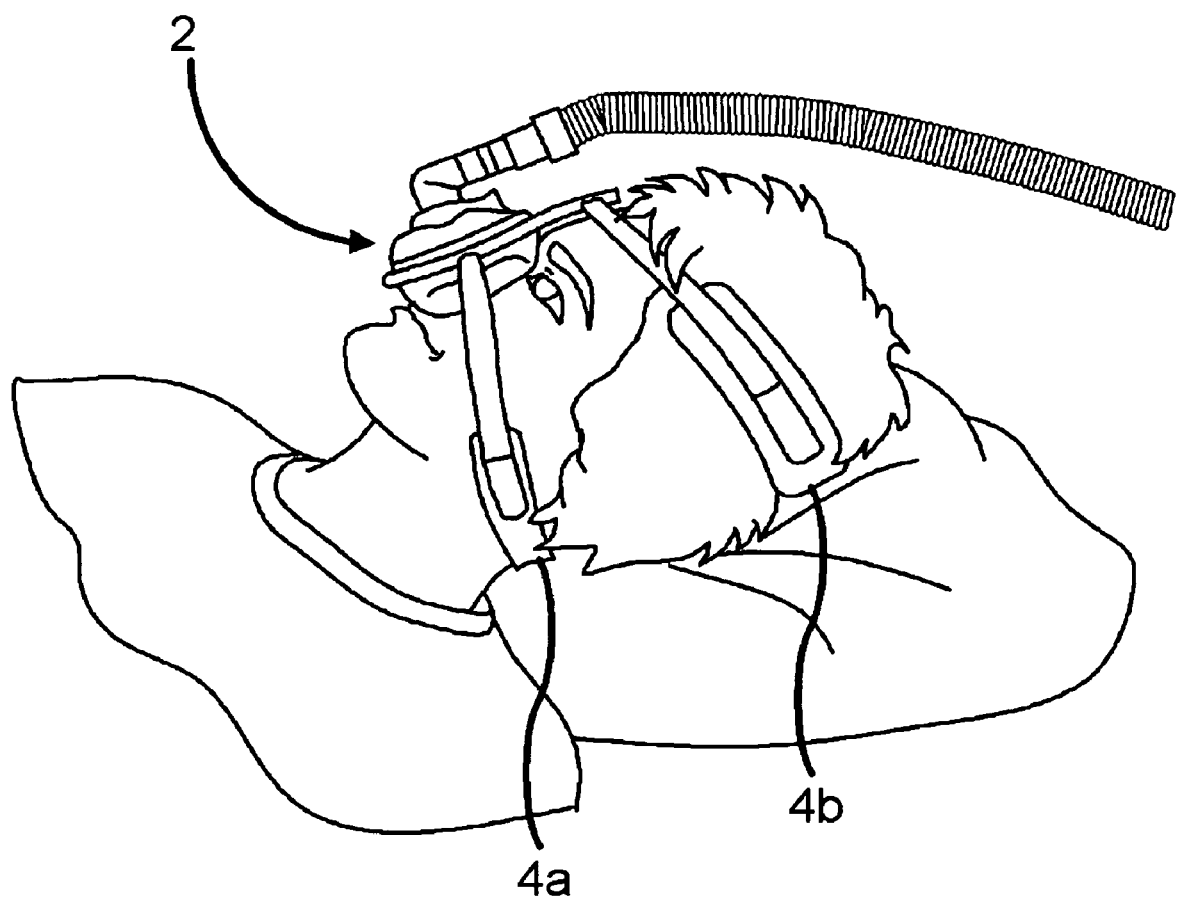
FIG. 1 is an exemplary diagram of a CPAP mask fitted to a user.

FIG. 1 shows an exemplary diagram of a CPAP face mask strapped tightly to the face of a patient. The CPAP mask system 2 is strapped to a patient's face using elastic bands 4a and 4b, covering the patient's nose and mouth. Elastic bands 4a and 4b are strapped tightly to the patient's face, ensuring that an air and/or liquid-tight seal may be formed between mask 2 and the patient's face. Consequently, the use of comfort cover utilizing moleskin or a similarly soft material will greatly increase the comfort of the patient. A similarly soft material could include any material that prevents or minimizes skin irritation.

Figure 2:
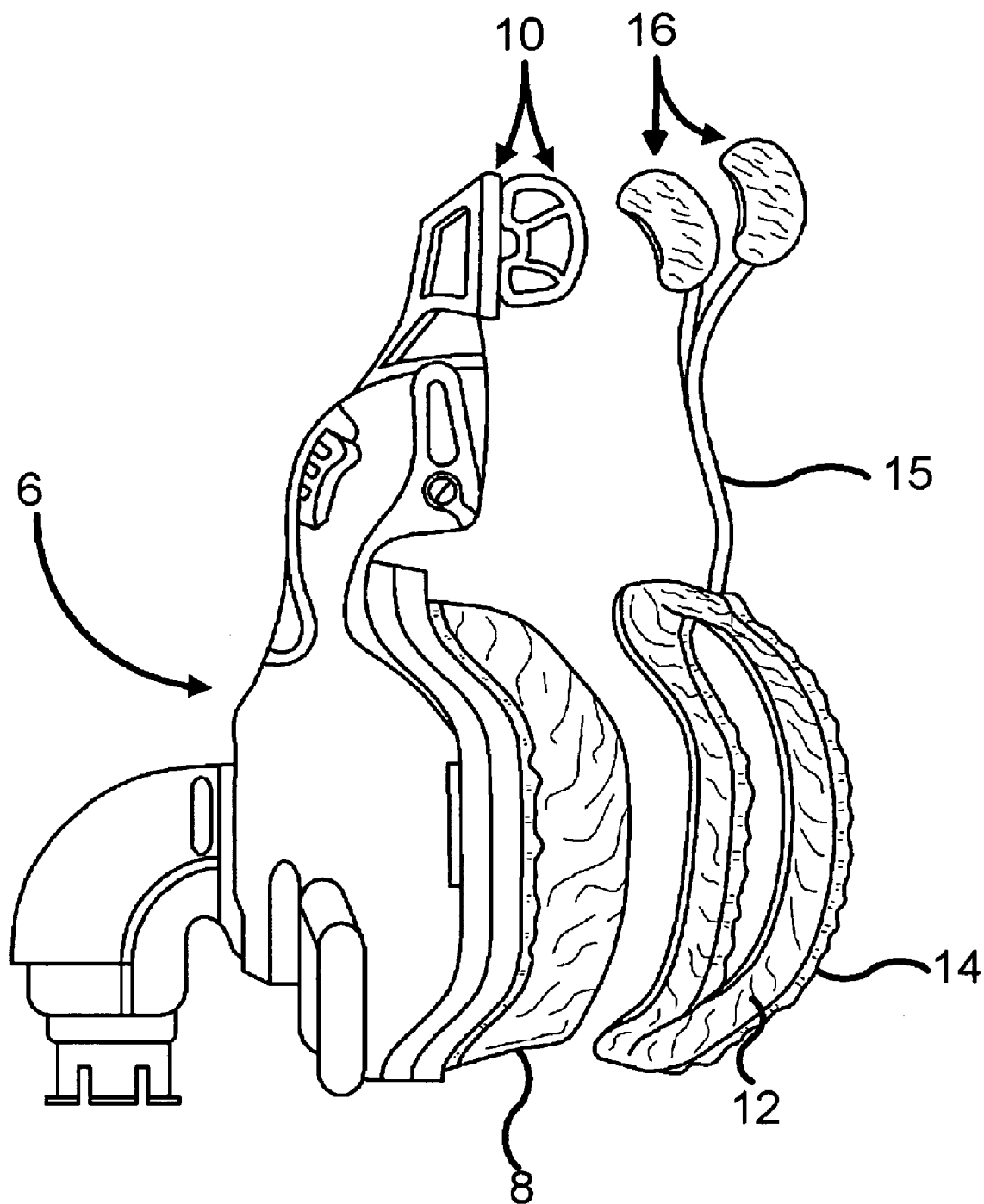
FIG. 2 is an exemplary side perspective diagram of a CPAP mask and the associated moleskin attachment.

FIG. 2 is a detailed exemplary diagram of a CPAP mask with a detached comfort cover. The mask 6 functions as previously described with respect to FIG. 1. Cushion 8 contacts the patient's face, allowing for an air and/or liquid-tight seal over the nose and mouth. Forehead pads 10 contact the patient's forehead, allowing for the mask to maintain a stable position and providing anchor points for a headband. In one embodiment, of the present invention, a comfort cover 12 utilizing moleskin or similarly soft material is formed in a shape matching the contour of cushion 8 so as to retain the air and liquid-tight seal of CPAP mask 6. An elastic band 14 is attached to the comfort cover 12 allowing for the material to be fastened to the cushion 8. Additionally, moleskin or a similarly soft material can be applied to forehead pieces 16, which are then mated with forehead pads 10 on the CPAP mask 6. The forehead pieces 16 may, optionally, be attached to the comfort cover 12 via a connector 15 or similar configuration. Likewise, the forehead pieces 16 may be independently mated with the forehead pads 10.

Figure 3:
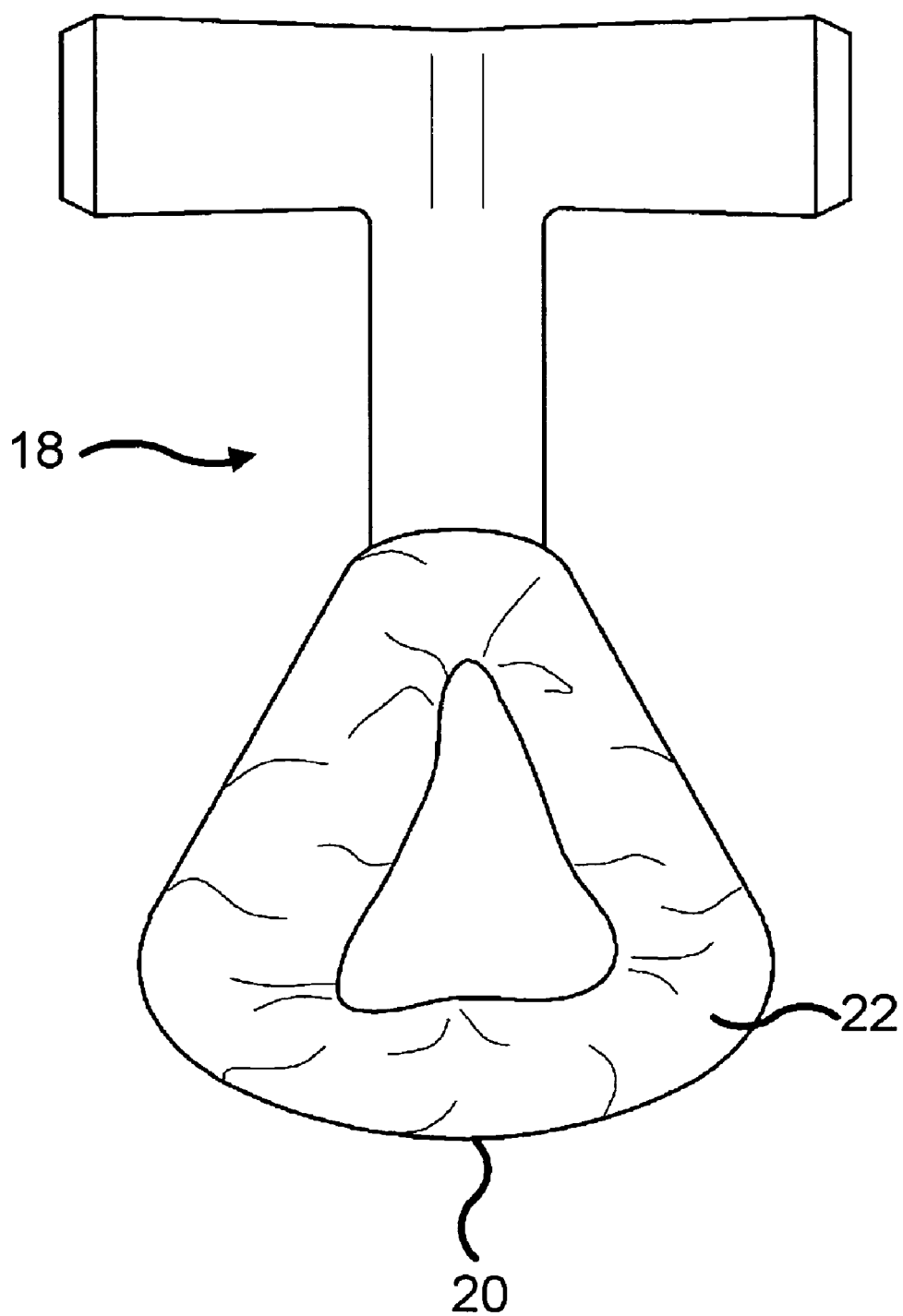
FIG. 3 is an exemplary rotated diagram of a ventilation mask with an attached moleskin covering.

FIG. 3 is a rotated view of a CPAP mask 18. The cushion 20 covering the patient's nose and mouth is shown under comfort cover 22, which incorporates moleskin, or a similarly soft material. The comfort cover 22 may be attached to the cushion using the elastic band 14 from FIG. 2. The use of the elastic band allows for the comfort cover 22 to mold to the contours of cushion 20, ensuring a tight seal between the patient's face and the mask. Further, the pliable nature of the moleskin on the comfort cover 22 ensures that the mask will comfortably fit the curves of the patient's face.

Figure 4:
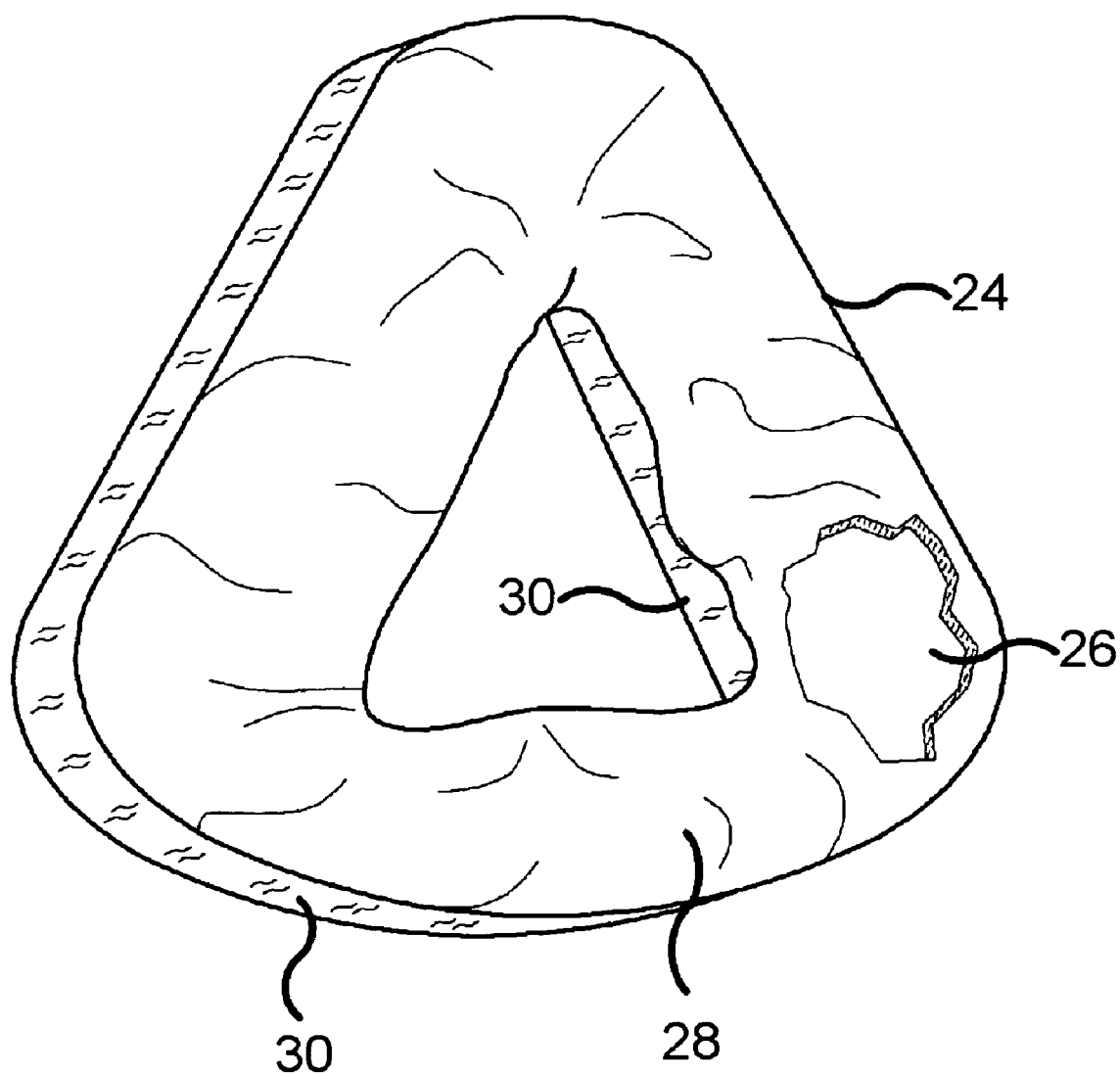
FIG. 4 is an exemplary diagram of a triangular ventilation mask with an attached moleskin covering.

FIG. 4 is another exemplary diagram of the cushion portion of a CPAP mask 24. Cushion 26 is shown in the cut out section of the mask 24. A comfort cover 28 completely covers the cushion 26 and matches the contours of the mask 24. Elastic band 30 is shown on the interior and exterior perimeters of mask 24. The elastic band covers the entire perimeter of the comfort cover 28 and allows the material to be securely fastened to mask 24. The elastic band also allows for the moleskin to be fastened to masks with slight variations in size and shape without losing the air and liquid-tight seal of the CPAP mask 24. Different shapes of CPAP masks, however, require matching the moleskin material's shape to that of the mask 24.

Figure 5:
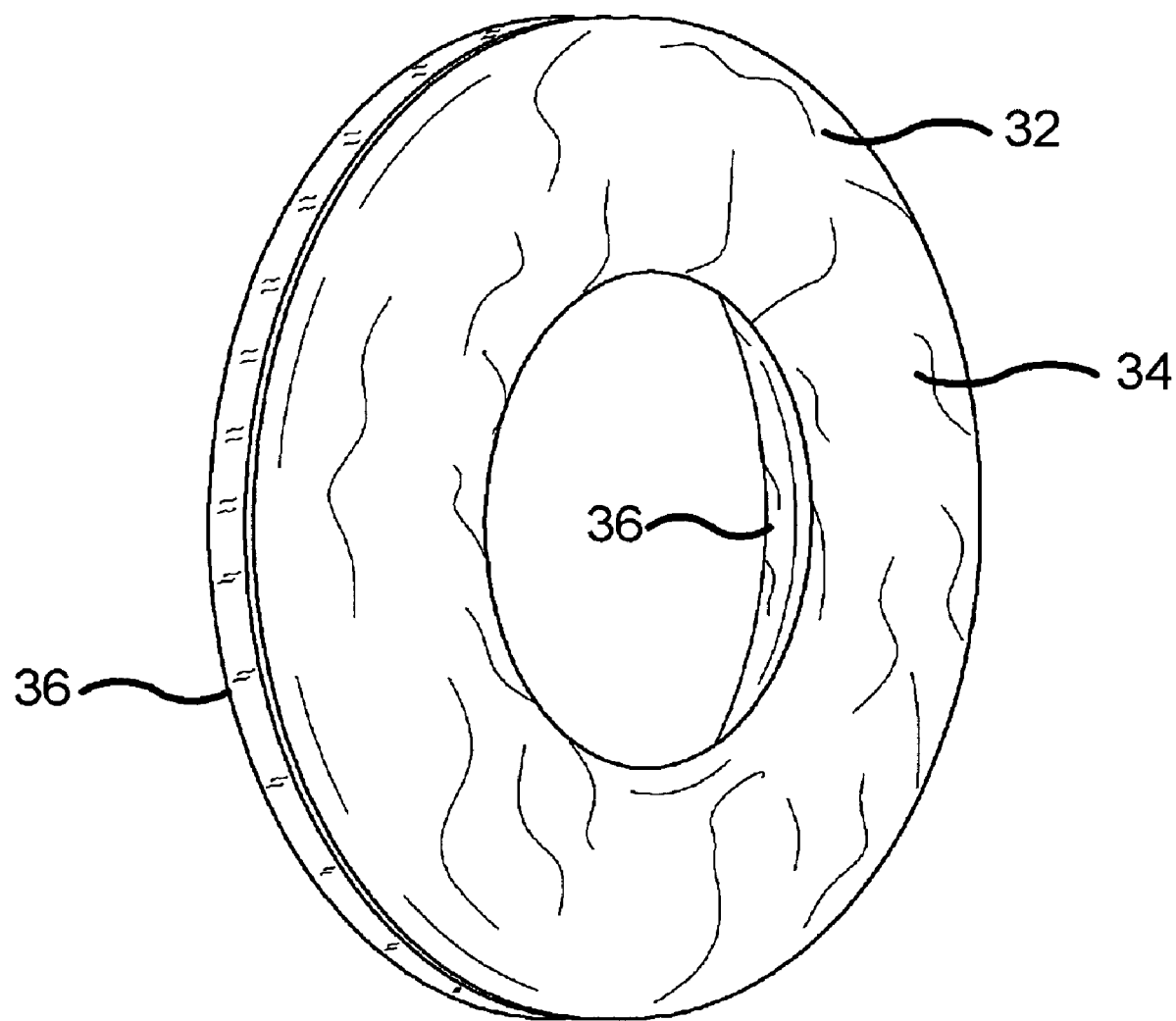
FIG. 5 is an exemplary diagram of a circular ventilation mask with an attached moleskin covering.

FIG. 5 shows a further embodiment of the present invention wherein the moleskin cover can be fashioned to fit a variety of mask shapes. In this embodiment, CPAP mask 32 is shaped in a circular or oval fashion, which deviates from the rounded triangular forms shown in FIGS. 1-4. However, for CPAP masks in this configuration, a comfort cover 34 can be made to fit around the mask. Further, elastic band 36 is again used to secure the interior and exterior perimeters of the moleskin cover 34 to the mask 32. Thus, moleskin cover 34 can be manufactured to fit over triangular masks, circular masks, or any other shape mask that wherein the features of the moleskin are desired.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit an scope of the appended claims.

The invention claimed is:

1. A ventilation interface, comprising:
    a first soft material configured to be replaceably coupled to a first cushion of a face mask that is configured to interface with a user's nose;
    a second soft material configured to be replaceably coupled to a second cushion of a face mask that is configured to interface with a user's forehead, wherein the face mask is configured to allow the intake and exhaust of gases;
    a connector connecting the first soft material and the second soft material, wherein the connector maintains connection with the first soft material and the second soft material when either the first soft material is uncoupled from the first cushion of the facemask or the second soft material is uncoupled from the second cushion of the facemask; and
    an elastic band coupled to a perimeter of the first soft material, wherein the first soft material is configured to be replaceably coupled to the cushion by the elastic band.

2. The ventilation interface of claim 1, wherein the first and second soft materials are moleskin.

3. The ventilation interface of claim 1, wherein the coupling of the first cushion and the first soft material combine with the mask to form an air-tight and liquid-tight seal between the mask and the nose of the user.

4. The ventilation interface of claim 1, wherein the first soft material and elastic band are formed in the shape of the first cushion.

5. The ventilation interface of claim 4, wherein the first soft material fits substantially flush to the first cushion of the mask.

6. The ventilation interface of claim 1, wherein the face mask is a CPAP face mask, wherein the coupling of the first soft material to the CPAP mask is made using the elastic band attached to the perimeter of the first soft material.

7. A method of providing comfort to a CPAP mask user, comprising:
    coupling a first soft material to a first cushion of the CPAP mask surrounding the user's nose;
    coupling a second soft material to a second cushion of the CPAP mask contacting the user's forehead;
    connecting the first soft material and the second soft material via a connector, wherein the connector maintains connection with the first soft material and the second soft material when either the first soft material is uncoupled from the first cushion of the facemask or the second soft material is uncoupled from the second cushion of the facemask.

8. The method of claim 7, wherein the coupling of the first soft material to the CPAP mask is made using an elastic band attached to the perimeter of the first soft material.

9. The method of claim 8, wherein the first and second soft materials are moleskin.

10. The method of claim 9, wherein the coupling of the first soft material to the first cushion forms and air-tight seal.

11. The method of claim 7 wherein the coupling of the first soft material is configured to be easily detached to allow replacement of the first soft material.

12. The method of claim 7, wherein the first soft material is formed to match the shape of the first cushion of the CPAP mask.

13. A method of applying a cover to a ventilation interface, comprising:
    forming a first comfort cover with an interior perimeter and exterior perimeter from a first soft material,
    forming a second comfort cover configured to contact a user's forehead with a second soft material,
    forming a connector configured to connect the first comfort cover with the second comfort cover, wherein the connector maintains connection with the first comfort cover and the second comfort cover when either the first comfort cover is uncoupled from the first soft material of the facemask or the second comfort cover is uncoupled from the second soft material of the facemask;
    connecting a first elastic band to the interior perimeter and a second elastic band to the exterior perimeter of the first comfort cover, and
    affixing the first comfort cover to the ventilation interface via the first and second elastic bands.

14. The method of claim 13, wherein the first and second elastic bands provide an airtight fit of the first comfort cover to the ventilation interface.

15. A means for increasing the comfort of a ventilation mask user, comprising:
    a first comforting means replaceably attached to a first portion of the ventilation mask that contacts the nose of a user, and
    a second comforting means replaceably attached to a second portion of the ventilation mask that contacts the forehead of a user;
    a connection means connecting the first comforting means with the second comforting means wherein the connection means maintains connection with the first comforting means and the second comforting means when either the first comforting means is uncoupled from the first portion of the ventilation mask or the second comforting means is uncoupled from the second portion of the ventilation mask.

16. The means for increasing comfort of claim 15, including an elastic means for securing the mask to the face of a user.

17. An apparatus for increasing the comfort of a ventilation interface, comprising:
    a first soft material formed in a manner that mirrors the user-side of the ventilation interface,
    a second soft material formed in a manner that contacts a user's forehead;
    an elastic band configured to secure the first soft material to the ventilation interface; and
    a connector formed in a manner that connects the first soft material with the second soft material wherein the connector maintains connection with the first soft material and the second soft material when the first soft material is unsecured from the ventilation interface.

18. The apparatus of claim 17, wherein the first and second soft materials are moleskin.

* * * * *